United States Patent [19]
Mojden et al.

[11] Patent Number: 5,158,424
[45] Date of Patent: Oct. 27, 1992

[54] AUTOMATIC TRAY LOADING, UNLOADING AND STORAGE SYSTEM

[75] Inventors: Wallace W. Mojden; Andrew Mojden, both of Hinsdale; Robert E. Darr, Chicago, all of Ill.

[73] Assignee: Fleetwood Systems, Inc., Countryside, Ill.

[21] Appl. No.: 866,113

[22] Filed: Apr. 7, 1992

Related U.S. Application Data

[60] Continuation of Ser. No. 544,683, Jun. 27, 1990, abandoned, Division of Ser. No. 449,304, Dec. 5, 1989, Pat. No. 4,979,870, which is a continuation of Ser. No. 195,220, May 18, 1988, abandoned.

[51] Int. Cl.$^5$ .............................................. B65G 57/24
[52] U.S. Cl. .................................... 414/799; 414/751; 294/87.1
[58] Field of Search ............ 414/416, 751, 753, 788.4, 414/788.8, 791.6, 788.2, 792.9, 798.4, 796.9, 799, 928, 933; 198/347; 294/87.1, 81.6, 81.61, 81.62

[56] References Cited

U.S. PATENT DOCUMENTS

| | | | |
|---|---|---|---|
| 4,505,636 | 3/1985 | Sugino et al. | 414/736 |
| 4,541,762 | 9/1985 | Tischler et al. | 414/796.9 X |
| 4,568,231 | 2/1986 | Czajka et al. | |
| 4,808,057 | 2/1989 | Chiappe et al. | |

FOREIGN PATENT DOCUMENTS 141938 1/1987 European Pat. Off. .

OTHER PUBLICATIONS

AEP Automatic End Packaging, The Sardee Corporation, The Canmaker, Feb., 1989, pp. 13-15.

Primary Examiner—Michael S. Huppert
Assistant Examiner—William M. Hienz
Attorney, Agent, or Firm—Trexler, Bushnell, Giangiorgi & Blacsktone, Ltd.

[57] ABSTRACT

An automatic loading and unloading system is provided for loading articles supplied from a first location at a rate commensurate with the rate at which articles are supplied from the first location into trays and for unloading the articles from the trays for transport to a second location at a rate commensurate with the demand for articles at the second location, and for balancing a supply of articles loaded onto trays with variations in both the rate of supply thereof and the rate of demand therefor. The system includes a tray loading station, and a tray loading apparatus for loading articles supplied from the first location into trays at tray loading station. An infeed device feeds articles to the loading apparatus in a predetermined, orderly fashion. At a stacking station, a stacking device stacks article-filled trays to form a supply thereof for use on demand. An outfeed device delivers articles on demand to the second location in a predetermined, orderly fashion. At an unloading station, an unloading apparatus unloads articles from article-filled trays to the outfeed device upon demand, such that article-filled trays may alternatively be stacked by the stacking device or delivered to the unloading station, in accordance with fluctuations in the supply and demand for articles at the first and second locations, respectively.

4 Claims, 15 Drawing Sheets

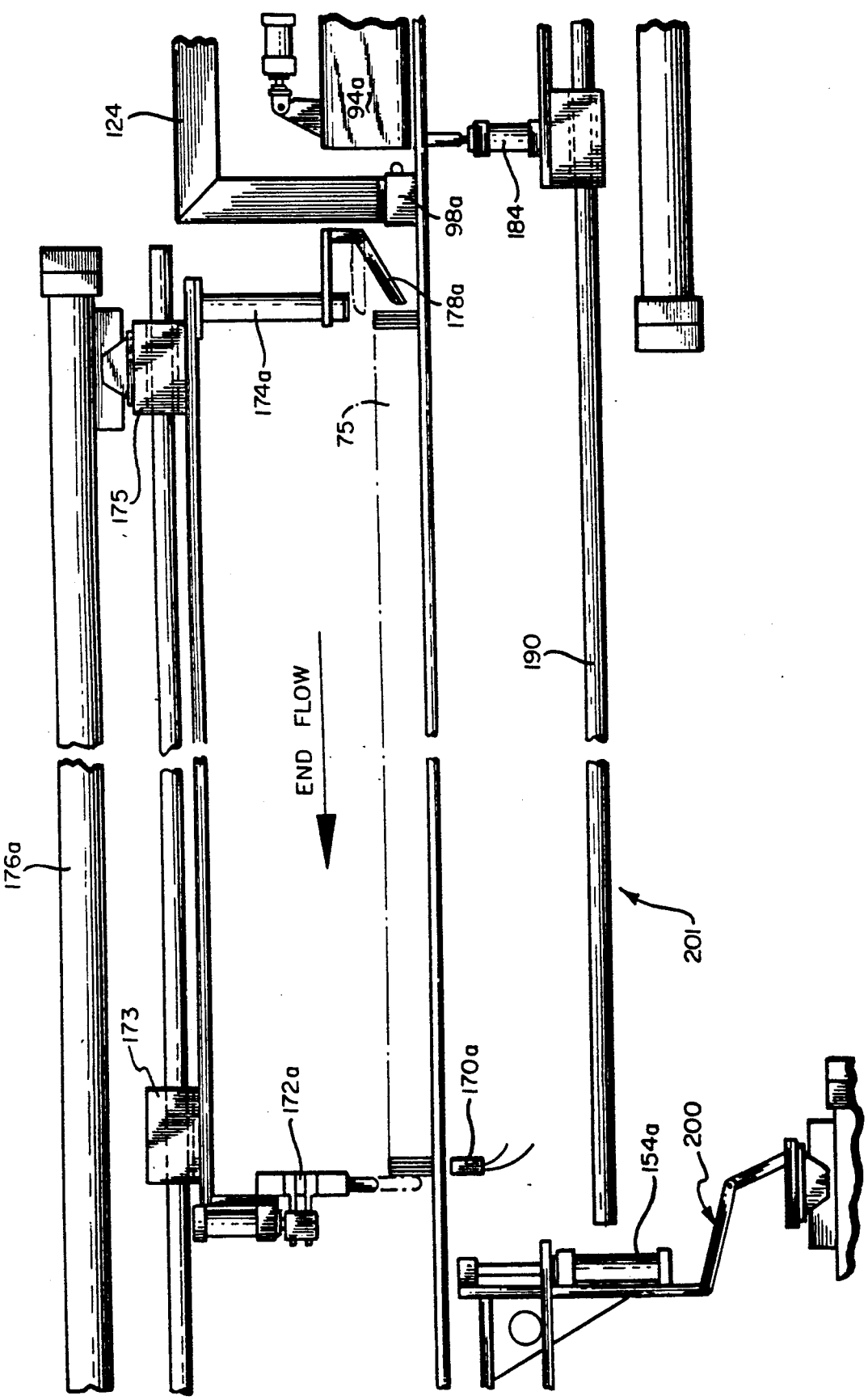

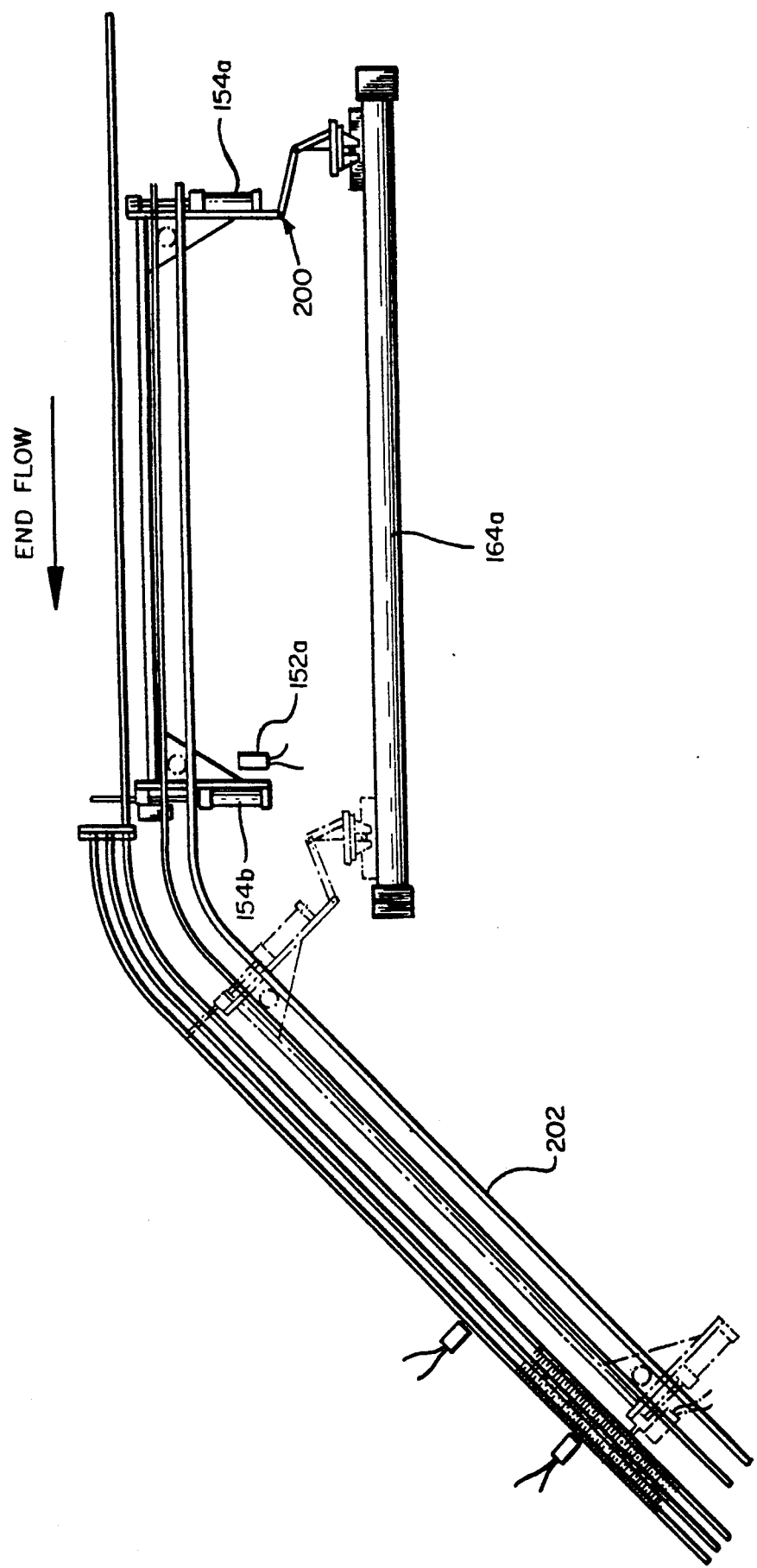

AUTOMATIC TRAY LOADING, UNLOADING AND STORAGE SYSTEM

This application is a continuation of application Ser. No. 07/544,683, filed Jun. 21, 1990, now abandoned, which is a division of Ser. No. 07/449,304, filed Dec. 5, 1989, now U.S. Pat. No. 4,979,870, which is a continuation of Ser. No. 195,220, filed May 18, 1988, now abandoned.

BACKGROUND OF THE INVENTION

This invention is directed to article handling apparatus, and more specifically to apparatus for loading and unloading a plurality of like articles with respect to a plurality of trays for storage and/or transport between various article handling and/or utilization stations.

While apparatus in accordance with the invention may find utility in a number of applications, the ensuing description will be facilitated by particular reference to a system for handling can ends.

In the manufacture of containers such as beverage cans or the like, a great number of can end parts are required. Generally speaking, modern aluminum beverage container bodies present but a single open end and hence require but a single end closure piece or "can end", as they are called in the trade. In any event, a number of apparatus have heretofore been devised for handling, stacking, packaging and unpackaging can ends during their manufacture and for further processing, both prior to and up to their final assembly with can bodies. A great number of individual steps or stations can be utilized in processing can ends prior to this final assembly. For example, at one stage the ends may be suitably cleaned and sterilized for use in beverage or other food containers. At yet another station some protective inner lining material or substance may be applied for use in some beverage and food container applications. Yet another operation may involve the fitting of pull rings to tear-away openings or the like, as in the case of so called "flip-top" or "pop-top" type containers.

Accordingly, modern container preparation and assembly operations require that numerous relatively small disk-like can ends be transported from one station to the next in a more-or-less continuous process up to, and including, the final assembly thereof with can bodies. Generally speaking, however, such final assembly does not take place until the filling of the container or body by the end user. Accordingly, separate processing of the ends and bodies prior to the filling process is generally contemplated.

It should also be appreciated that modern can ends have a slight curl or lip, as well as the frequently present tear-away top portion with graspable tab, ring, or the like. The lips or curls tend to make can ends nestable in generally flat, coaxial side-by-side arrangement. However the tabs or rings tend to cause the can ends to tilt or cant somewhat. That is, the graspable tabs or rings for removing the tear-away opening tend to impart a spring-like action to a stack of otherwise nested or closely axially placed ends, which tends to cause the ends to spread apart somewhat and at least the endmost members to tilt or cant, or perhaps come apart entirely from the remaining members of a stack.

Furthermore, it has become important to provide a reasonably accurate count of can ends for handling in individual, predictably-sized groups or, as they are called in the art "sticks". It should be appreciated that modern operations require that on the order of hundreds and sometimes even thousands of ends be processed per minute to maintain the desired efficiency of operation. Accordingly, it will be appreciated that the accurate and rapid handling of large numbers of groups or sticks of can ends is an important consideration in achieving such efficient operation. Needless to say, errors in counting and handling and transporting such can end sticks or groups can damage equipment and/or cause a shutdown of extremely large and expensive processing systems or factories. The attendant delay can be extremely costly in terms of idle personnel and machinery, as well as in terms of delayed processing of parts, such as by causing failure to meet required delivery dates or the like.

Accordingly, we have devised novel and patented machinery and other apparatus for facilitating the accurate and rapid handling of large numbers of can ends. Examples of these modern can end handling systems are shown for example in a number of prior patents which are assigned to the assignee of this application, for example: Mojden et al. U.S. Pat. Nos. 3,165,218; 3,337,064; 3,523,602; 3,545,631; 3,595,372; 3,618,550; 3,878,945; 3,722,741; 3,754,635; 4,000,709; 4,364,466; 4,537,010; 4,537,550; and 4,580,938.

We have now developed a novel and improved automatic tray loading and unloading and storage system for can ends, which advantageously is adapted in effect, to "balance" the supply and flow of can ends as between one station and the next in a multiple station processing plant as described hereinabove. Advantageously, our system greatly facilitates the overall balancing of the operations between various stations by permitting automatic loading of ends upon processing thereof at one station onto standard pallet-sized trays, which may then be readily transported by normal pallet handling methods and apparatus to one or more other stations for further processing of the can ends.

Advantageously, our system permits ready storage of excess can ends from one station until they are needed for further processing at other stations. Hence, any oversupply or shortage developed because of a shutdown or slow down of one station in a multiple station operation need not affect the continued operations of the remaining stations. Hence, our novel system permits a relative balancing of the operations in a multiple station processing plant to thereby optimize the efficiency of operation within the plant. In effect, our system accommodates varying rates of supply of can ends as they are delivered from any given processing station with different and also varying rates of demand for can ends at other processing stations. That is, any excess supply is absorbed, and any shortage is made up, by our system.

OBJECTS AND SUMMARY OF THE INVENTION

Accordingly, it is a general object of the invention to provide an automatic tray loading and unloading system for use in a multiple station article processing operation.

A more specific object is to provide an automatic tray loading and unloading system for accommodating and balancing operations among multiple stations in a multiple station can end processing and handling facility.

Briefly and in accordance with the foregoing objects, the invention comprises an automatic loading and unloading system for loading articles supplied from a first location at a rate commensurate with the rate at which articles are supplied from said first location, into trays and for unloading said artricles from said trays for transport to a second location at a rate commensurate with the demand for said articles at said second location, and for balancing a supply of articles loaded onto said trays with variations in both the rate of supply thereof and the rate of demand therefor, said system comprising: a tray loading station; tray loading mean for loading said articles supplied from said first location into trays at said tray loading station, infeed means for feeding said articles to said loading means in a predetermined, orderly fashion; a stacking station; stacking means for stacking article-filled trays to form a supply thereof at said stacking station for use on demand; outfeed means for delivering said articles on demand to said second location in a predetermined, orderly fashion; an unloading station; and unloading means for unloading said articles at said unloading station from said article-filled trays to said outfeed means upon demand, such that article-filled trays may alternatively be stacked by said stacking means or delivered to said unloading station, in accordance with fluctuations in the supply of, and demand for. articles at said first and second locations, respectively.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

FIG. 17 is a somewhat simplified view of a second stage of an outfeed apparatus, broken at the middle for ease of illustration; and FIG. 18 is a somewhat simplified side elevation of a discharge apparatus which may advantageously be used in connection with the outfeed appartatus.

DETAILED DESCRIPTION OF THE ILLUSTRATED EMBODIMENT

Figure 1:
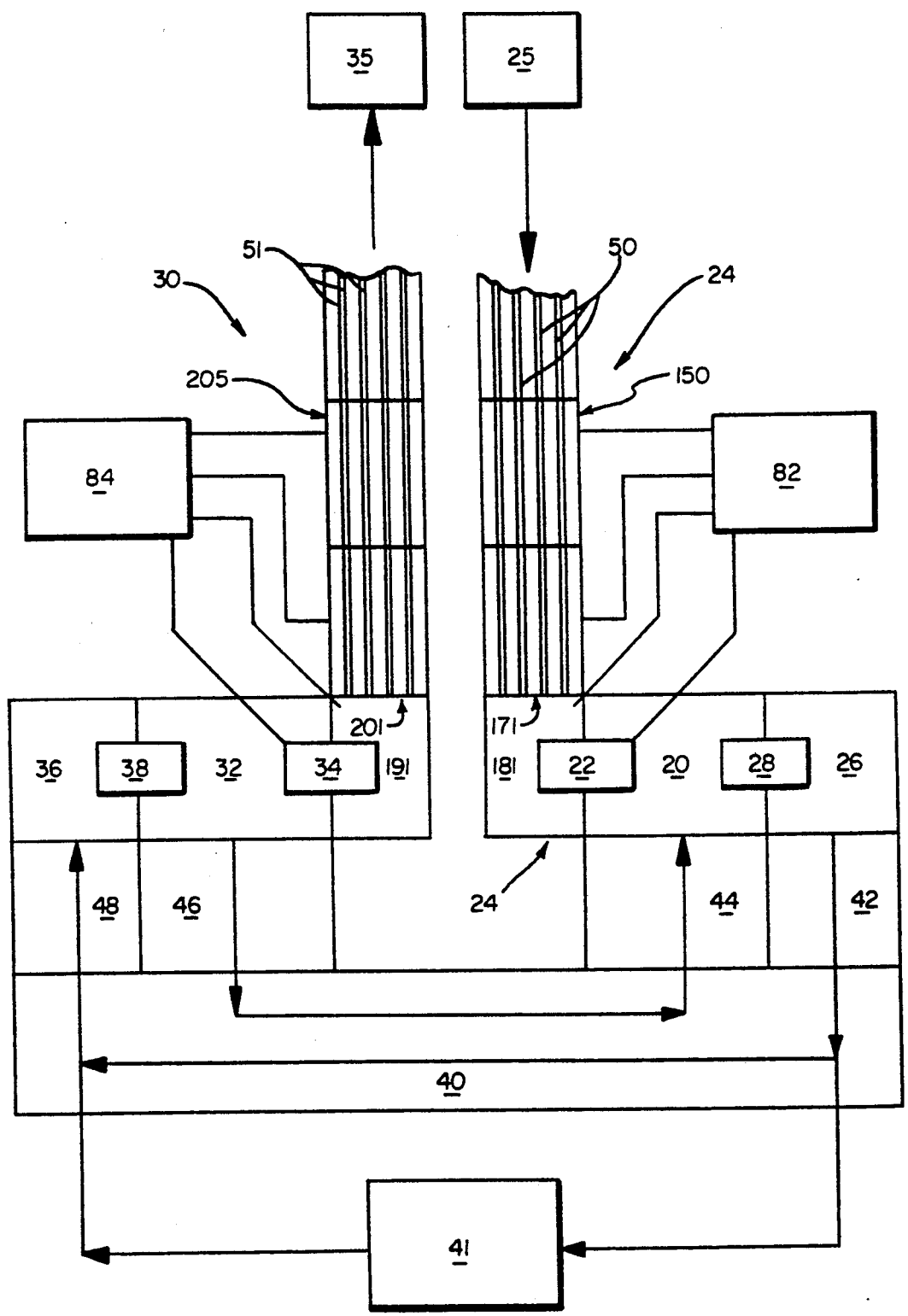
FIG. 1 is a simplified diagrammatic illustration of an automatic tray loading, unloading and storage system in accordance with the invention.

Referring now to the drawings and initially to FIG. 1, there is illustrated an automatic loading and unloading system for loading and unloading articles, such as can ends. These articles are supplied from a first location 25, and are loaded into trays 55 at a rate generally commensurate with the rate at which they are supplied from the first location. The system also unloads the articles from the trays 55 for transport to a second location 35 at a rate generally commensurate with the demand for articles at the second location, while advantageously balancing a supply of articles loaded onto the trays 55 with variations in both the rate of supply thereof and the rate of demand therefor. The system of the invention is shown in a somewhat simplified, diagrammatic form in FIG. 1.

The system includes a tray loading or filling station 20 and tray loading means 22 for loading the articles which are supplied from the first location 25 into initially empty trays 55. Adjacent the tray filling station 20 is an infeed means 24 to be described in detail later herein, for feeding the articles as they are supplied from the first location 25 to the loading means 22 in a predetermined, orderly fashion. A stacking station 26 is also located adjacent the tray loading station 20 and stacking means 28 are provided for stacking article-filled trays to form a supply thereof at the stacking station 26 for use on demand.

As the articles are called for at a second location 35, they are supplied thereto by outfeed means 30 of the apparatus of the invention, in a predetermined, orderly fashion as demanded by the location 35. An unloading station 32 is provided at which unloading means 34 transfer or unload articles from the article-filled trays 55 to the outfeed means 30 upon demand. Accordingly, it will be seen that article-filled trays may be stacked by the stacking means 26 then delivered to the unloading station 32, in accordance with fluctuations in the supply of articles from the first location 25 as well as in the demand for articles at the second location 35.

As shown in FIG. 1, the system of the invention also preferably includes an unstacking station 36 at which unstacking means 38 deliver individual article filled multi-pocketed or multi-channeled trays 55 to the unloading station 32 for unloading thereat. Accordingly, some means such as conveyor means 40 may also be provided for conveying or transporting the article-filled trays 55 between the stacking station 26 and the unstacking station 36. Moreover, this conveyor or conveyor means 40 is preferably reversible such that empty trays from the unloading station 32 may likewise be transported to the tray loading station 20 for reuse and refilling. Alternatively, filled trays may be removed from the stacking station 26 or the conveyor 40 and transported to a suitable storage location 41 to be held for use later as desired.

It will be appreciated from the foregoing discussion that the system already described in general terms is capable of taking up any excess in the supply of articles from the first location 25 by either stacking filled trays at stacking station 26 and/or unstacking station 36 or alternatively by moving the excess trays off to storage location 41. Similarly, the system thus far described is capable of satisfying any increases in the demand for articles at the second location 35 by feeding additional trays of articles to the unloading station either from the stacking and/or unstacking station or from the storage location 41.

In the embodiment shown in FIG. 1 additional feeder conveyor means 42, 44, 46 and 48 are also illustrated for transporting filled and empty trays respectively from and to the reversible conveyor 40. Preferably these feeder conveyors run between the conveyor 40 and the stacking station 26, the unstacking station 36, the filling or loading station 20, and the unloading station 32, respectively, to thereby transport respective filled and empty trays between these stations and the conveyor 40, as described above. Transport of the trays from the stations to the conveyors may occur manually, by means of a forklift truck, or in similar fashion, within the use of complicated automated handling equipment.

Figure 2:
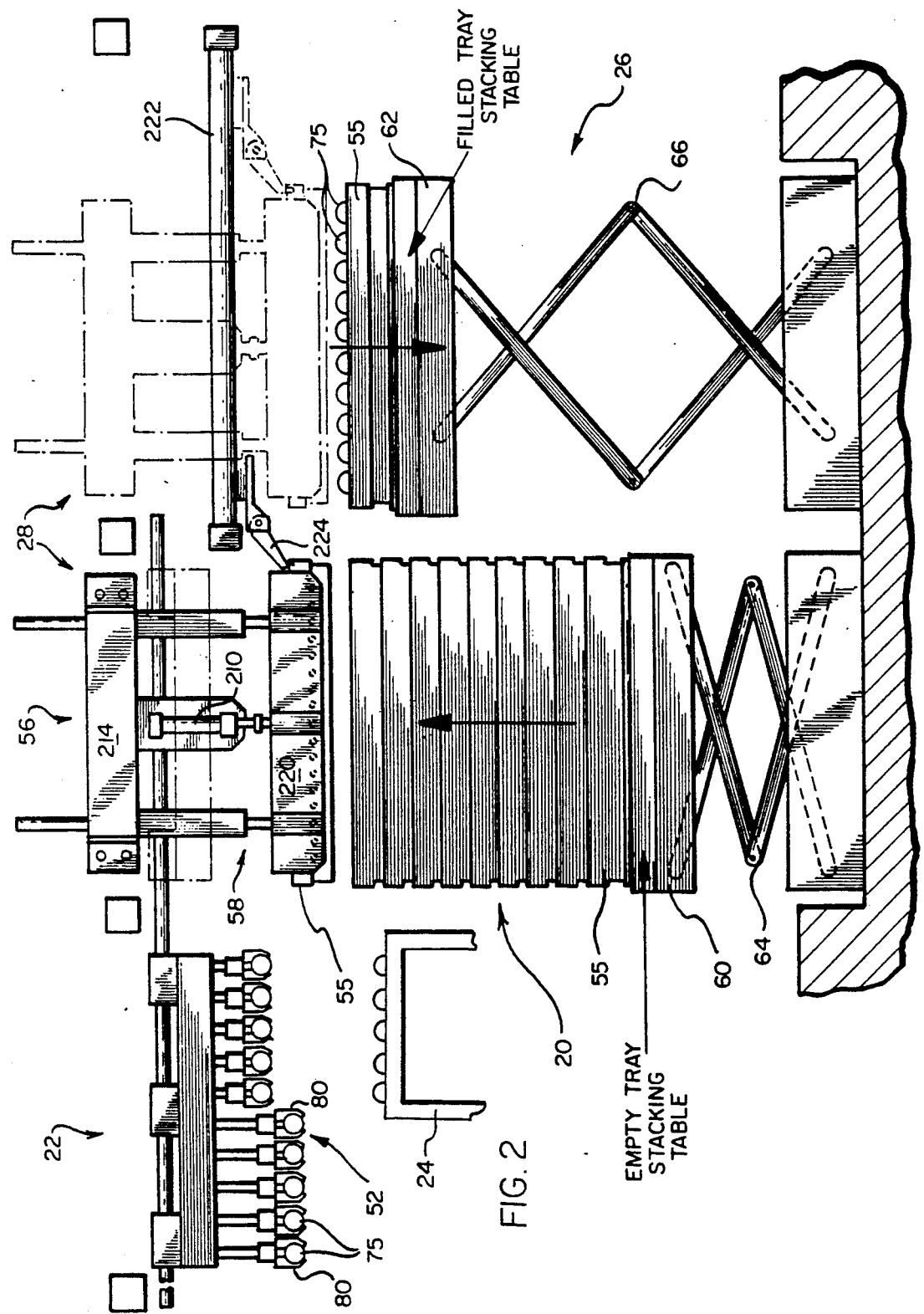
FIG. 2 is a perspective view, also somewhat diagrammatic in form, illustrating respective infeed, tray loading and tray stacking stations of the system of FIG. 1.

Reference is now also invited to FIG. 2, in connection with which some further description of the infeed and outfeed means will be given. Generally speaking, the infeed and outfeed means are substantially identical apparatus, although arranged for transporting the articles or can ends in opposite directions. Hence for purposes of simplicity of description, only the infeed means 24 is shown in FIG. 2. It is to be understood however, that the outfeed means 30 is of a similar structure and design. This infeed (and also the outfeed) means comprises at least one, and preferably a plurality of, generally parallel side-by-side elongate lanes or trough-like members 50 (51 at the outfeed side) for receiving and transporting the articles in a generally linear direction and in a generally linear alignment.

Figure 3:
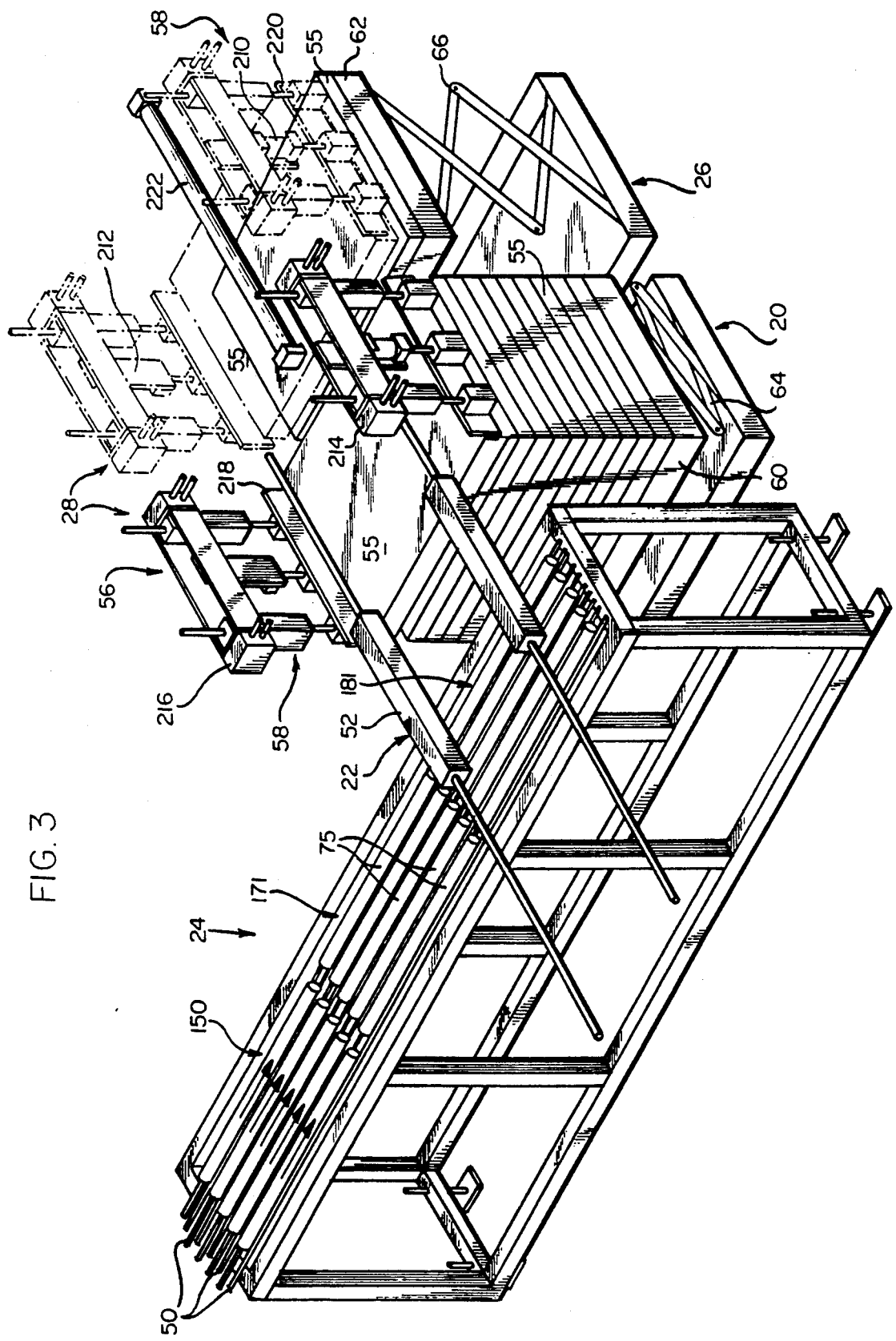
FIG. 3 is an end elevation of a major portion of the apparatus of FIG. 2, illustrating some further details thereof.
Figure 4:
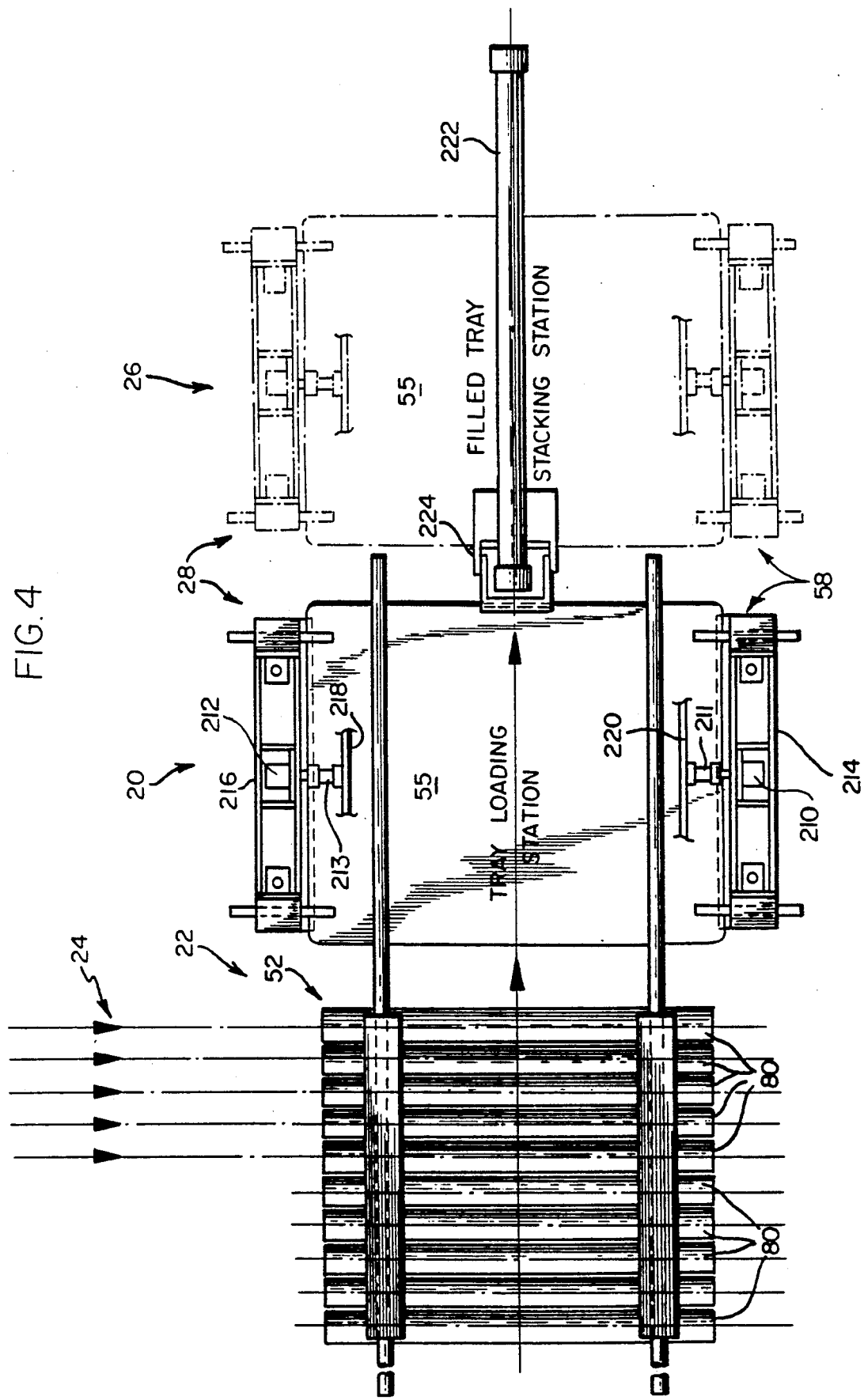
FIG. 4 is a top plan view of the apparatus of FIG. 3.

Accordingly, the loading means and the unloading means each comprise substantially identical pick-and-place devices or units, generally designated by reference numerals 52 and 54, further details of which are illustrated in FIGS. 3 and 4, to which reference is also invited. Only the loading means devices 52 are shown in FIGS. 3 and 4, it being understood that the unloading means devices 54 are substantially identical. Still further details of the pick-and-place units or devices will also be described later herein with reference to FIGS. 9 through 14.

Suffice it to say at present that these pick-and-place devices 52 are adapted to respectively engage the articles in infeed lanes 50, to transport the engaged articles and to place them in empty trays at the tray loading station 20. On the other hand, substantially identical pick-and-place units or devices 54 (not shown in FIGS. 2-4) are provided with respect to the tray unloading station 32 for retrieving articles from the filled trays, for transporting these articles and for placing the articles into the lanes 51 of the outfeed means 30. Thereupon, the pick-and-place units or devices 52, 54 are adapted for disengaging the articles and returning for further articles to be respectively loaded and unloaded relative to the trays.

As best viewed in FIG. 3, the respective stacking and unstacking means further comprise respective palletizing and depalletizing means or devices located respectively at the stacking and unstacking stations. These palletizing and depalletizing means or devices are identical with respect to the stacking and unstacking stations, whereby only one such device or means 56 is illustrated in FIG. 3, in connection with the filled trays stacking station 26. This palletizing means or device includes a lift and transport device 58 which lifts filled trays from an empty tray stacking table 60 to a filled tray stacking table 62 adjacent and to one side thereof. In this regard, FIGS. 2-3 show the lifting and transporting unit 58 illustrated in both positions to indicate this action.

Accordingly, each of the tray stacking tables 60, 62 includes suitable means such as a scissors-like lifting and lowering arrangement 64, 66 to index trays upwardly so as to present an empty tray for filling by the pick-and-place means 52 at the tray loading station 20, and to off-load a filled tray, respectively. Conversely, the scissors-like or other suitable lifting and lowering devices 64, 66 index downwardly as additional trays are stacked one upon the next thereover. It should be appreciated that similar lift-and-transport device and tray stacking tables at the unstacking station 36 and tray unloading station 32 will be substantially identical, to those illustrated in FIGS. 2-4. That is, at the unloading station, a filled tray stacking table will move upwardly as filled trays are removed therefrom and an empty tray stacking table will move downwardly as successive trays are placed thereupon to be emptied by the associated unloading pick-and-place device. As discussed hereinabove, the empty trays may be removed from the empty tray stacking table at the unloading station 32 for transport back to the loading station to be refilled, as desired. Similarly, filled trays may be transported from the stacking station 26 to the unstacking station and particularly to the filled tray stacking table thereof as required during operation of the system and of the associated first and second locations being balanced or accommodated by the system.

It should further be recognized that the infeed lanes may receive articles such as can ends from a plurality of different stations, machines or other areas where a similar operation has been performed thereupon. Similarly, the outfeed lanes 30 may comprise a number of separate lanes for feeding a plurality of second locations, stations or machines which utilize the ends supplied from the respective first location or locations. Hence, the diagrammatic showing of FIG. 1 has been greatly simplified for ease of illustration and description herein.

Referring now also to FIGS. 9 through 15, the structure and operation of the pick-and-place means, devices or units 52 will be described in some further detail. Some occasional reference may also be had to various details of the configuration of the trays 55, as best viewed in FIGS. 5 and 6. As previously indicated, the respective infeed and outfeed means each preferably comprises a plurality of similar elongate lanes or trough-like members 50 for receiving the articles (such as can ends) in generally linear, coaxial fashion. Moreover, as is the practice in the can end handling arts, the can ends are generally handled in groups of axially closely spaced or nested ends, referred to in the art as "sticks". Each of these sticks of ends must be held in a relatively closely nested condition to avoid tilting or other displacement of individual ends within the group, which can result in one or more ends being misaligned or even missing from a group. This can in turn result in the entire group, in effect, falling apart, and the attendant difficulty with loose articles interfering with machinery, etc. Also, such a sudden loss of one or more ends from a stick can cause shutdown of an entire factory, or substantial portions thereof, while the necessary clean-up operation is completed, to avoid possible damage to expensive equipment and machinery.

Figure 13:
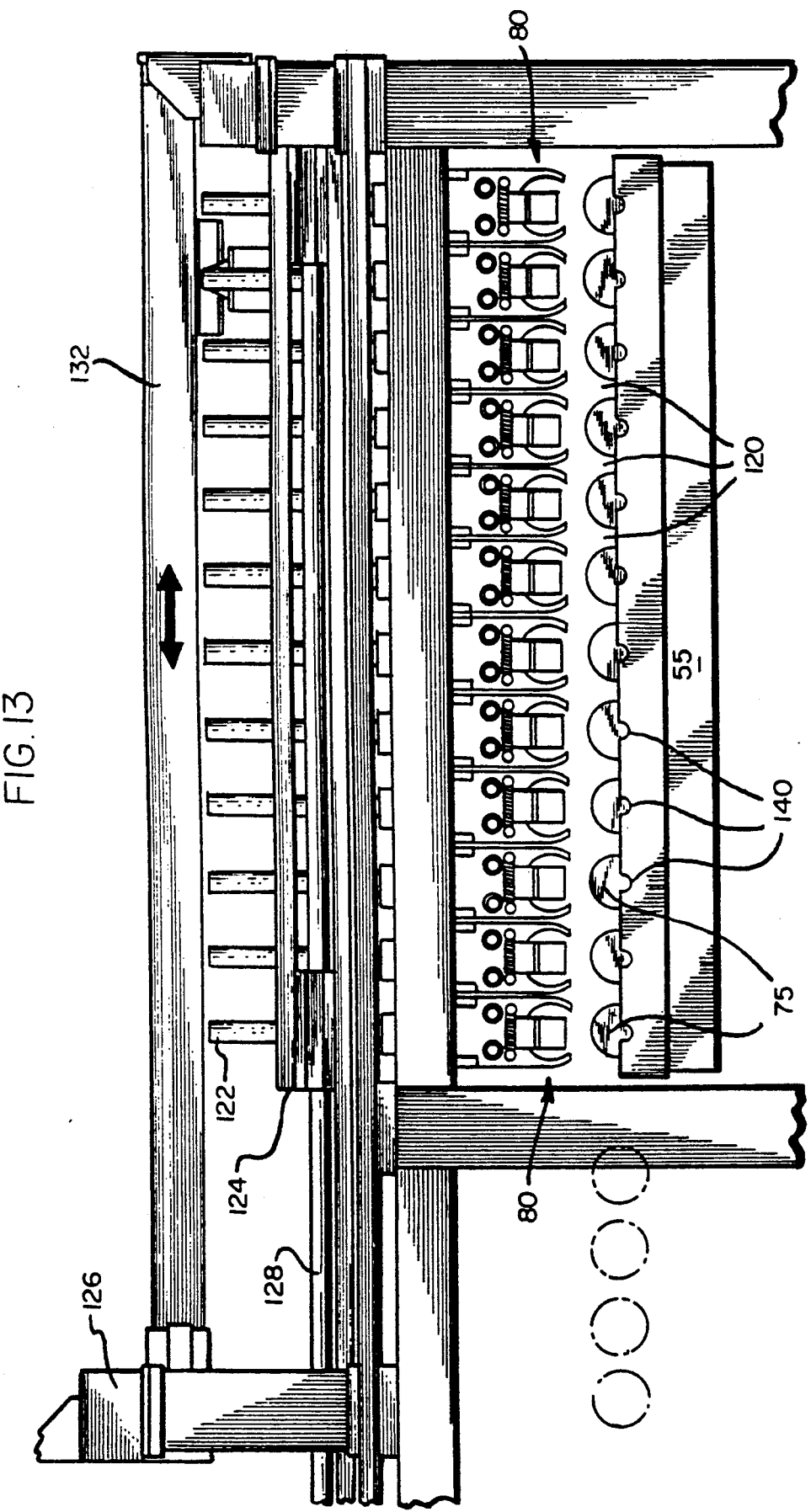
FIG. 13 is a partial end elevation showing a plurality of pick-and-place units, together forming the loading and/or unloading means of the invention, in connection with frame members and drive members for mounting and actuating the same and a somewhat simplified view of a tray member filled with can ends to be handled thereby.
Figure 14:
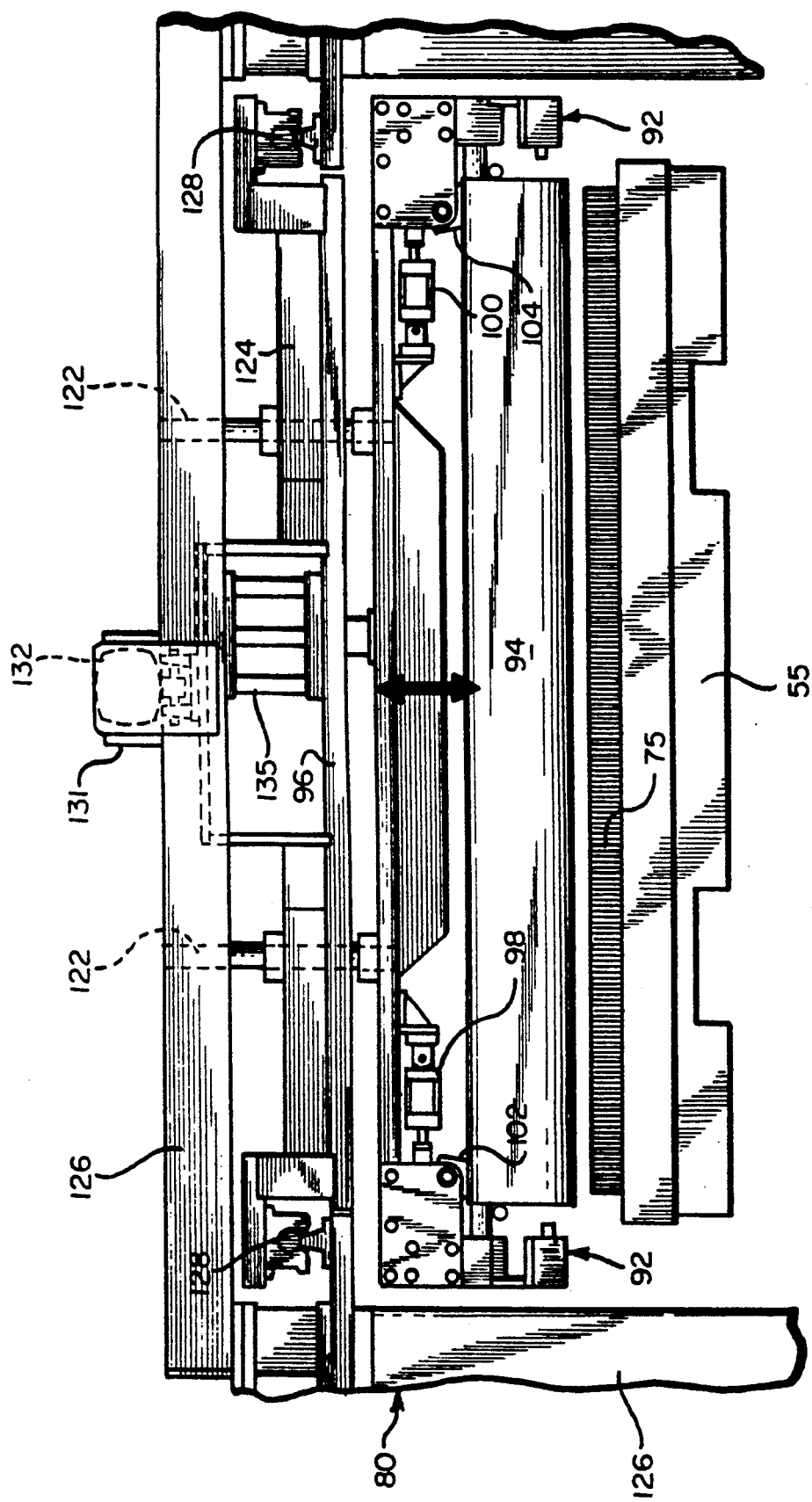
FIG. 14 is a side elevation of the showing of FIG. 13.
Figure 15:
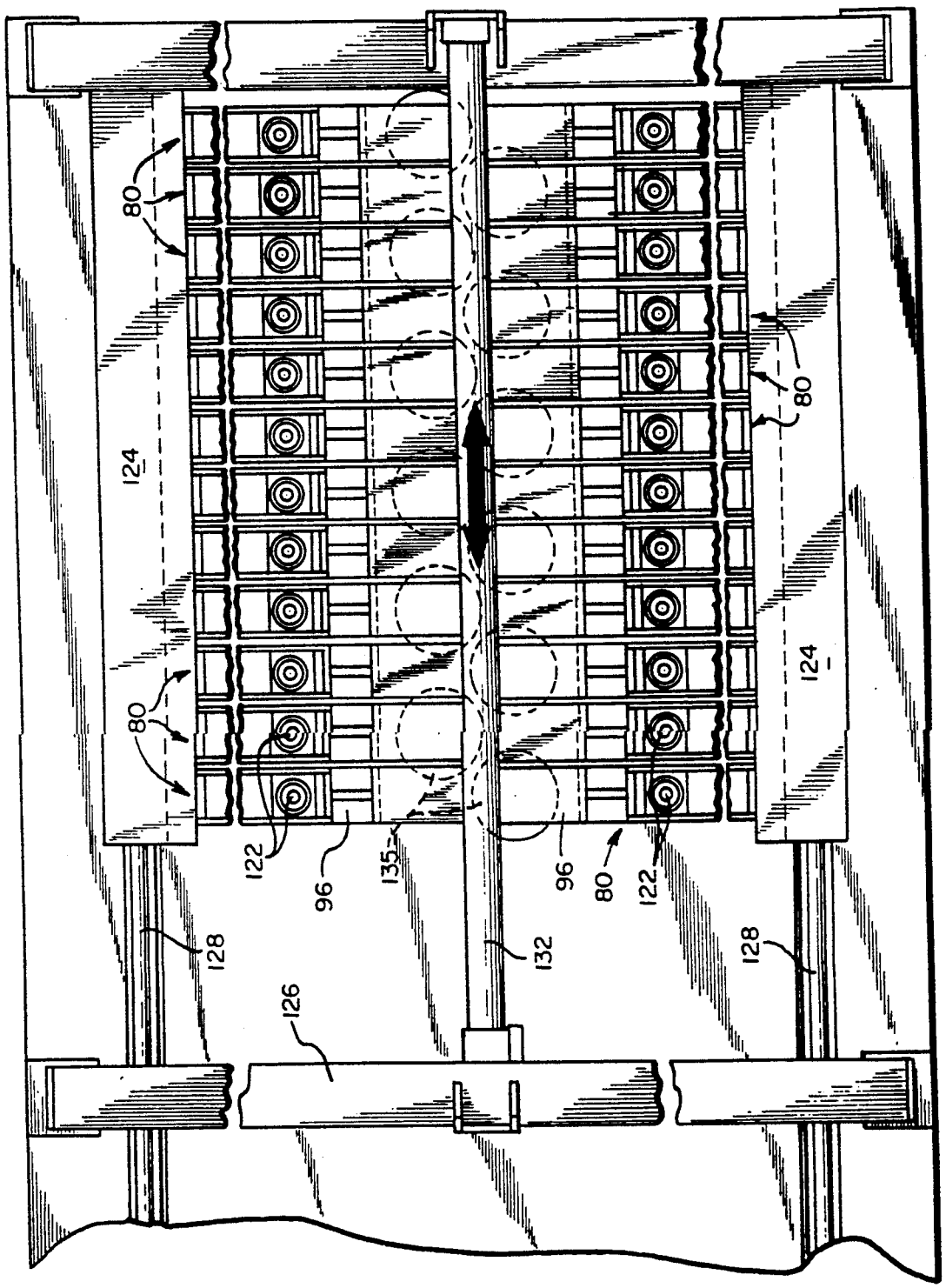
FIG. 15 is a top plan view of the showing of FIGS. 13-14.

Accordingly, and referring to FIGS. 3 and 13, the pick-and-place devices 52 generally comprise individual pick-and-place units or devices arrayed in a generally parallel arrangement to generally correspond to the number of groups of articles or "sticks" which are accommodated by each of the trays 55. In the embodiment illustrated in FIG. 3, it is contemplated that each tray will accommodate a total of ten parallel groups of articles. In FIG. 13, an embodiment for handling up to twelve parallel groups or sticks is illustrated. The individual pick-and-place devices are here designated by reference numeral 80. Each pick and place device or unit 80 is preferably individually controllable for retrieving a group of articles or stick of can ends from any filled one of the infeed lanes 50. Similarly, each pick-and-place unit or device 80a may be separately controlled to place a group of articles or stick of can ends in any empty one of the outfeed lanes 51. In this regard, like parts of the unloading pick-and-place unit 80a, shown in FIG. 16, are designated by like reference numerals with the suffix a.

More specifically, the pick-and-place devices 80, 80a are individually conrollable relative to both the infeed and outfeed lanes for locating and aligning with filled ones of the infeed lanes and empty ones of the outfeed lanes. This process is repeated until all of the parallel pick-and-place devices 80 have either retrieved articles from the infeed lanes and hence are all filled with articles, or on the other hand until all of the pick-and-place devices 80a have unloaded articles into the outfeed lanes and hence all are emptied of articles. On the other hand, the structure of the invention provides for operation of all of the pick-and-place devices 80 simultaneously, once all are filled, for depositing the articles simultaneously in all rows of a tray 55 for filling the same in a single operation. Conversely, the pick-and-place devices 80a are simultaneously operated in like fashion for simultaneously retrieving articles from a filled tray 55, preparatory to depositing these retrieved articles into the outfeed means or lanes 51. To this end, suitable control means 82, 84 (shown in diagrammatic form in FIG. 1) are provided for controlling the individual operation of the pick-and-place devices with respect to the infeed and outfeed lanes 50, 51.

Figure 9:
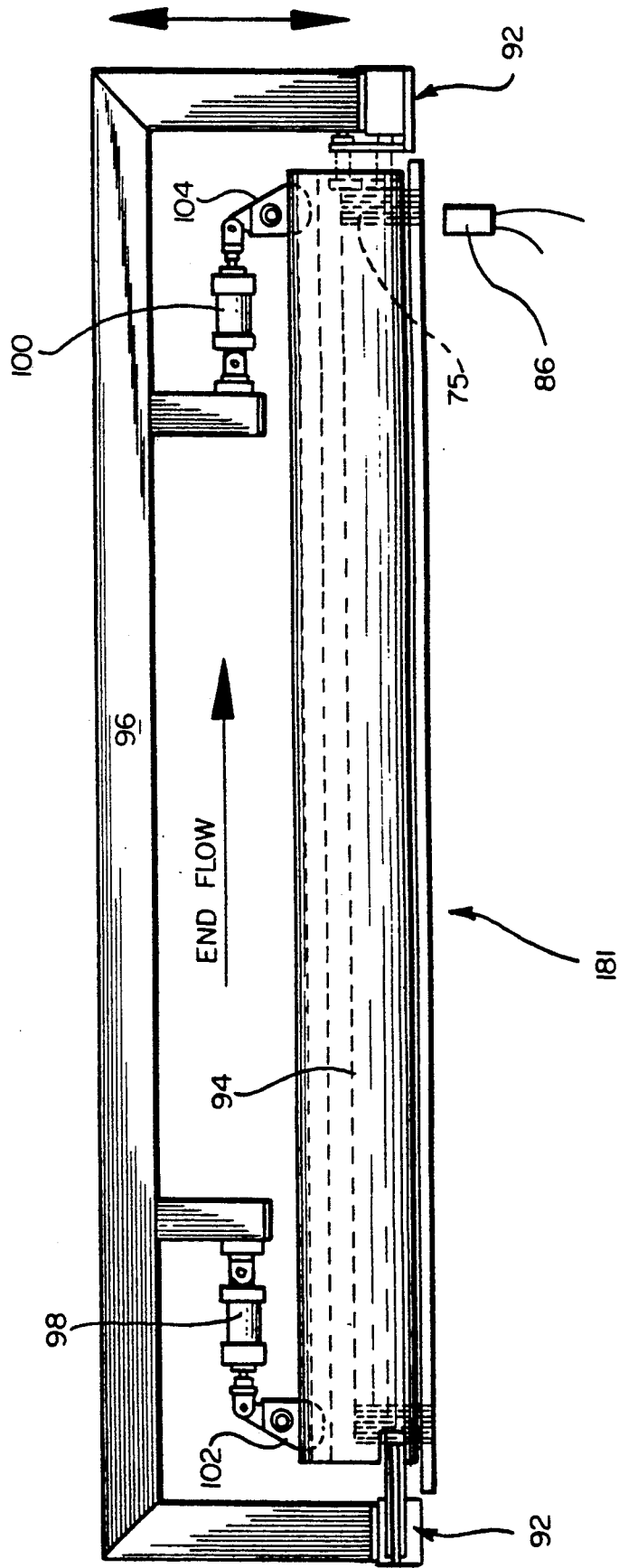
FIG. 9 is a somewhat simplified side elevation of a third stage or portion of the infeed apparatus, together with a simplified side elevation of a pick-and-place apparatus or unit forming a part of the tray loading and unloading means of the invention.
Figure 10:
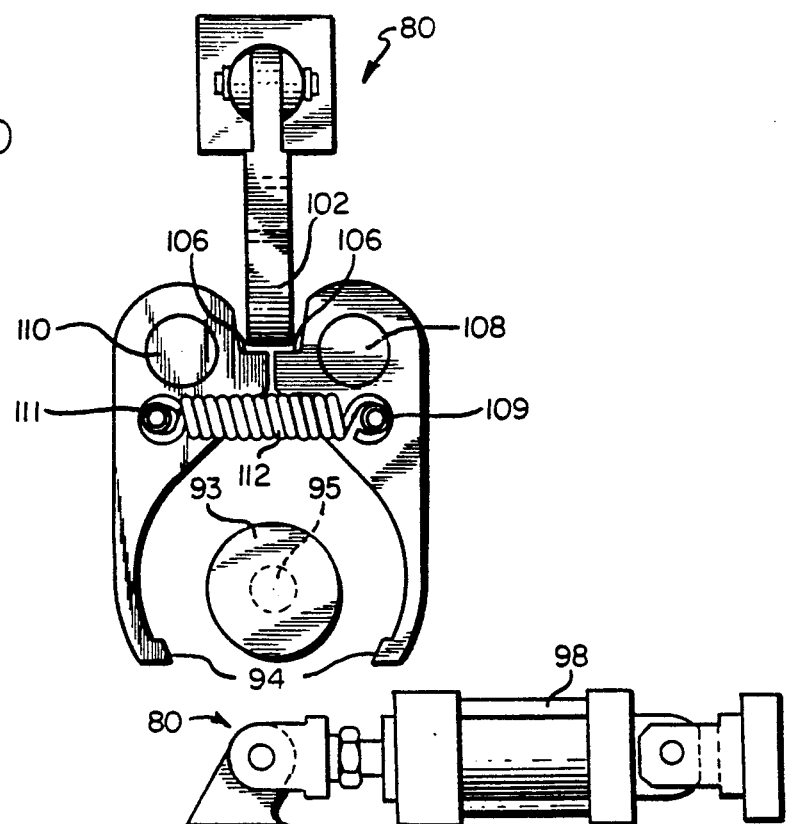
FIG. 10 is an enlarged partial view illustrating some further details of the pick-and-place apparatus.
Figure 16:
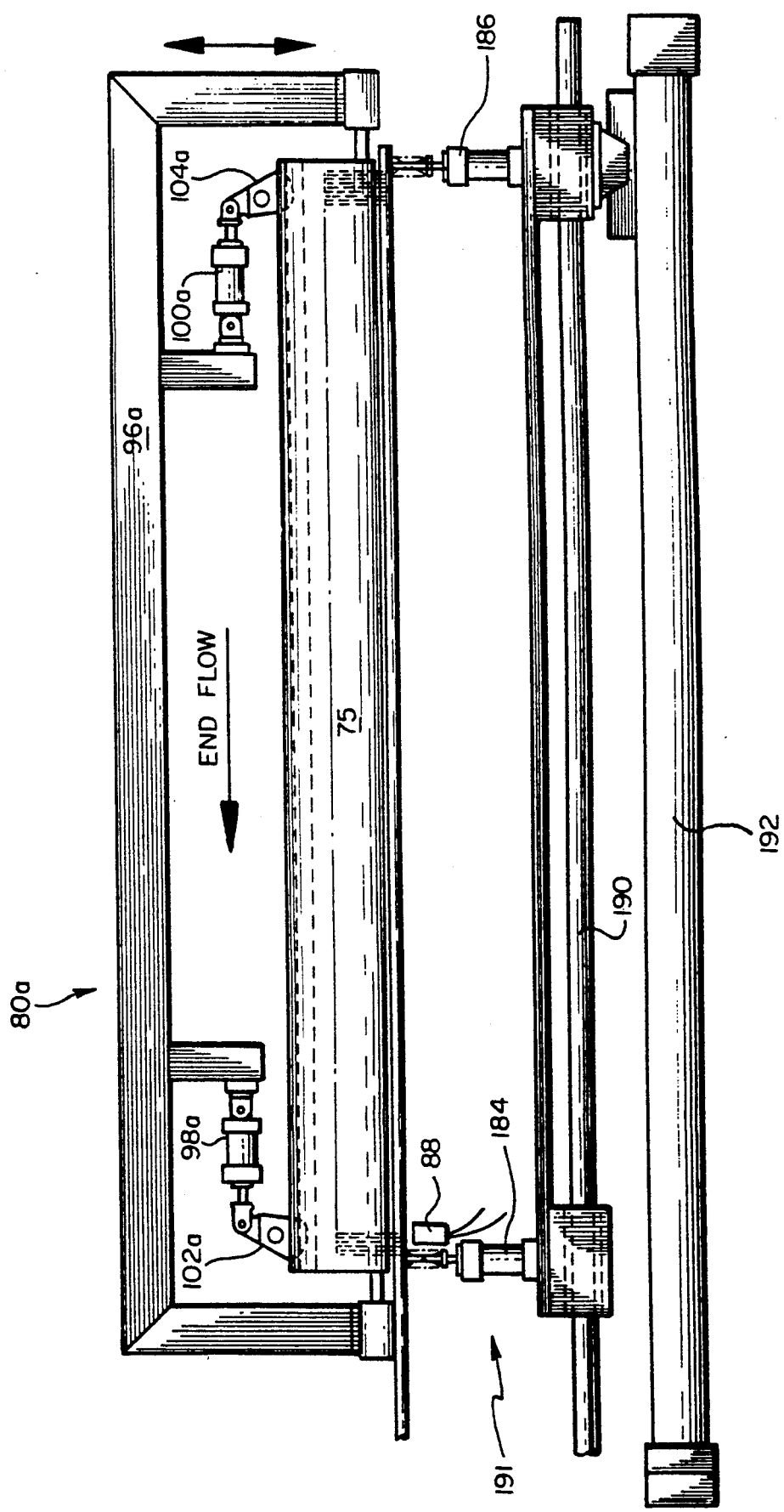
FIG. 16 is a somewhat simplified side elevation, similar to FIG. 14, showing delivery of can ends to a first stage of an outfeed apparatus of the type diagrammatically indicated in FIG. 1.

In this regard, and as best viewed in FIGS. 9 and 16, article presence or absence sensors 86, 88 are provided respectively at each of the infeed lanes 50 and outfeed lanes 51 for determining which lanes are filled with articles and which lanes are empty. The control means 82, 84 are therefore responsive to the control signals developed by these sensors 86, 88 for controlling the individual pick-and-place devices for retrieving groups of articles from the filled ones of the infeed lanes and for delivering articles to the empty ones of the outfeed lanes, respectively. Accordingly, the movement for alignment or "indexing" of individual pick-and-place devices or units 80, 80a over individual ones of the infeed and outfeed lanes, respectively, continues until all of the pick-and-place units 80 are filled with respect to the infeed lanes and ready to load an empty tray on the one hand, and until all of the pick-and-place units or devices are emptied and ready to return to a filled tray with respect to the outfeed means or side.

Referring now also to the details of the pick-and-place means or units shown in FIGS. 10-15, each unit 80 comprises a gripping portion or means 90 for simultaneously gripping all of the members of each group of articles or stick of can ends. These gripping means 90 generally take the form of a pair of elongate, arcuately shaped arms or jaw-like members 94 which generally surroundingly engage at lateral edges thereof, all of the members of a coaxially aligned groups of articles, such as a nested stick of can ends. The pick-and-place unit also includes respective oppositely axially inwardly directed pressing means or members 92. These members 92 are arranged for pressing inwardly upon opposite axial ends of each group of articles or stick of can ends within the gripping means or portion 90 to thereby securely hold a group of articles or stick of can ends tightly axially nested within the gripping means or jaws 90. In this regard, a typical such group of can ends or stick has been designated by reference numeral 75.

Figure 11:
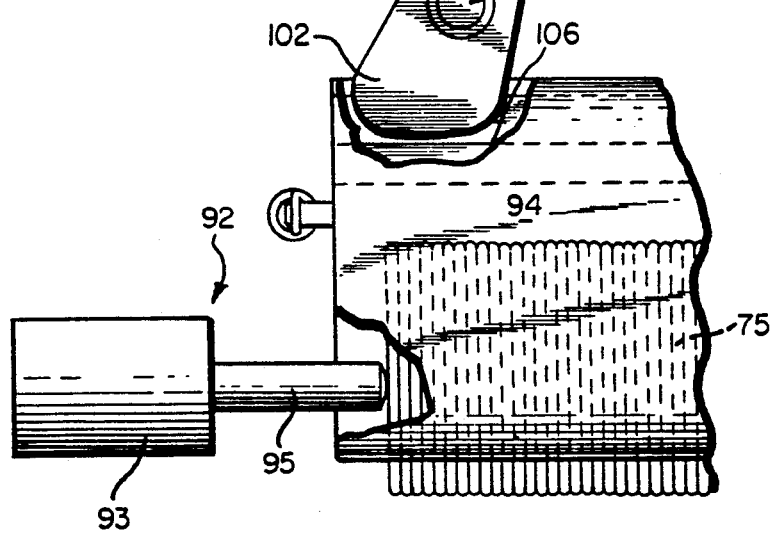
FIG. 11 is an enlarged partial end view of the pick-and-place apparatus.
Figure 12:
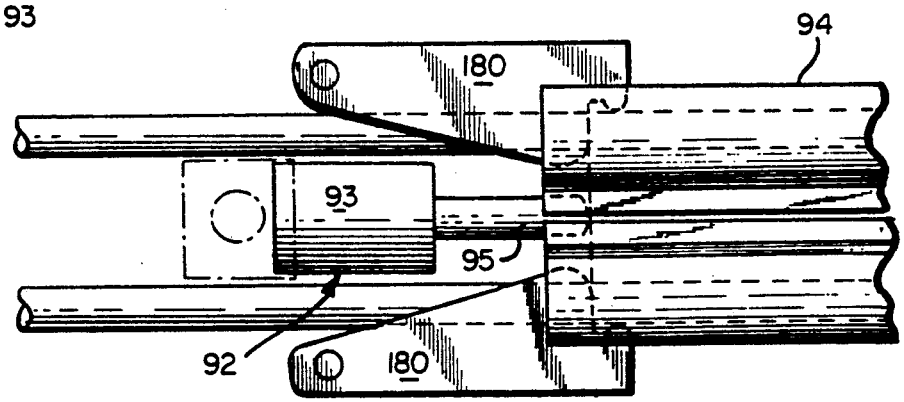
FIG. 12 is an enlarged partial side elevation of the pick-and-place apparatus.

In the illustrated embodiment, the article pressing means 92 include respective air cylinders 93 which drive pistons 95, and which are mounted at generally axially opposite ends of an elongate frame member 96 (FIG. 14) which also mounts the gripping means or portion 90. This gripping means or portion 90 will be seen to comprise, in addition to the gripping members or jaws 94, a pair of oppositely directed piston-and-cylinder drive means or members 98, 100, which are arranged for extending and retracting one end of each of a pair of pivotally mounted cams or cam-like members 102, 104. These cam-like members 102, 104, as best viewed in FIGS. 11 and 12, are arranged for pivoting at pivots 99 and for bearing against complementary cam surfaces such as surfaces 106 of the gripping member jaw portions 94. These jaws 94 are in turn pivotally mounted at pivots 108, 110. Finally, a tension spring 112 joins these two pivotally mounted jaw portions 94, at pins 109, 111 spaced from the pivots 108, 110, to urge the jaws in a direction for closing.

Accordingly, it will be seen that the at-rest or inactive position of the jaws is generally the closed position, as effected by spring 112 and as illustrated in FIG. 11. Hence, in order to open the jaws either to surroundingly engage or to release a group of articles or stick of can ends, actuation of the respective air cylinders 98, 100 and respective activation of the cam 102 for pressing the jaws outwardly against the tension of the spring 112 is required.

Figure 5:
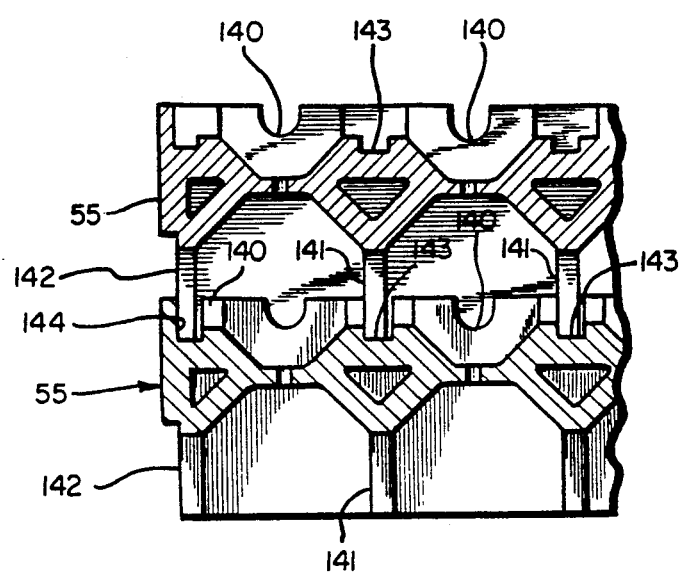
FIGS. 5 and 5A are partial sectional views of a tray member useful with the apparatus of the invention, FIG. 5A being enlarged somewhat.
Figure 6:
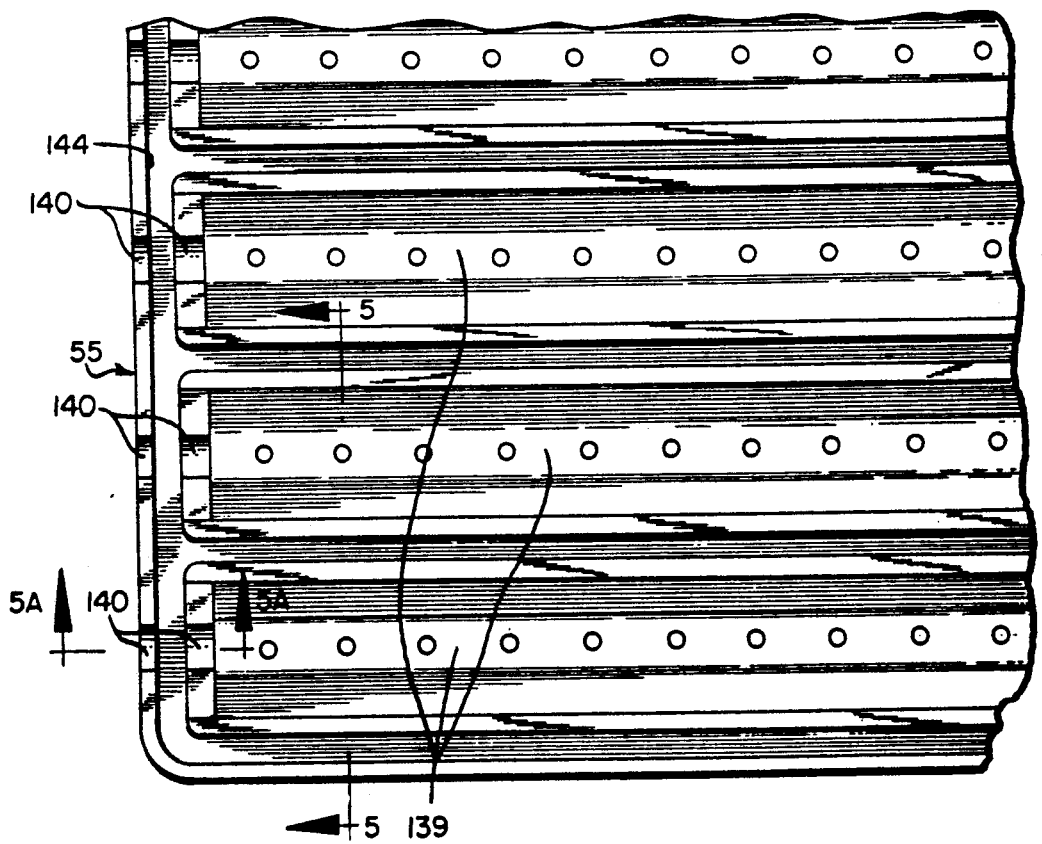
FIG. 6 is a partial top plan view showing further details of the tray, and also indicating the views of FIGS. 5 and 5A, generally along lines 5—5 and 5A—5A.

As best viewed in FIGS. 5, 6 and 13, the trays 55 are configured for cooperative operation with the gripping means and axial pressing means just described. In particular, and referring first to FIG. 13, it will be seen that the trays provide sufficient clearance space intermediate respective groups of articles, as indicated, for example by reference numeral 120, to permit the adjacent parallel gripping jaw members sufficient clearance to enter the tray and to open the jaws for surroundingly engaging the respective sticks 75 of can ends, without interferring with each other. Hence, sufficient clearance space is provided in the trays for simultaneously loading and unloading all of the groups of articles with respect thereto by the pick-and-place units or devices acting in unison, as previously described. To this end, the pick-and-place devices are mounted for individual motion on separate mounting shafts 122 with regard to a first sub-frame member 124, while the sub-frame member 124 is in turn mounted for simultaneously lifting and lowering all of the pick-and-place unit depending therefrom upon operation of a main frame 126.

Moreover, sub-frame 124 is fixed for horizontal motion along a pair of elongate shafts or bars 128, to thereby permit horizontal indexing of the respective pick-and-place units 80, 80a with respect to the infeed lanes 50 and outfeed lanes 51 as discussed hereinabove. An overhead track 1 31 mounts to frame assembly 126. A plurality of lift and lower, "pancake"-type cylinders 135 lift and lower each unit 80 individually with respect to frame 124.

Preferably, the horizontal motion and indexing of the pick-and-place units is controlled by a piston and cylinder arrangement such as an Origa cylinder 132 mounted in track 131. The Origa cylinder suspends frame 124 from one or more trolleys 133. In this regard, one particular useful such device for accommodating such a range of motion with the necessary degree of accuracy to permit indexing of the pick-and-place units with respect to the individual lanes is produced by Origa Corporation, 928 Oak Lawn, Elmhurst, Ill. 60126 under the designation Origa electric cylinder.

Figure 5A:
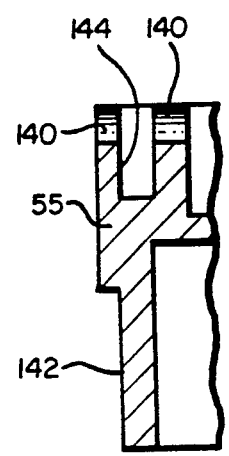

The trays (see FIGS. 5, 5A and 6) have individual pockets or channels 139, each for accommodating one "stick" of can ends. In order to accommodate the respective pressing members or air cylinders 92, a number of respective notches or cut-out portions 140 are provided in the tray 55 proximate the ends of the respective pockets or channels 139. Further, in accordance with a preferred feature of the invention, and as best viewed in FIGS. 5, 5A and 6, the trays are configured for nesting with respect to each other to facilitate the stacking or palletizing thereof at the tray stacking and unstacking stations 26, 36. In this regard, it will be seen that the outer end surfaces of the trays 55 have a stepped-back configuration at a lower portion thereof, as indicated at reference numeral 142 and a pair of spaced apart walls 144 of complementary configuration for receiving the stepped back portion 142, at a top portion thereof, to accommodate this nesting. It should be noted that each of the wall members or portions 144 are notched or apertured to provide the apertures 140 for receiving the piston-like pressing portions 95 of the air cylinders 92, as noted above. Additional internal struts 141 ar accommodated by recesses 143 to provide additional support and "resting" of the respective trays 55.

Referring now to FIGS. 7 through 10 and FIGS. 16 through 18, a preferred form of a typical lane 50, 51 the infeed and outfeed means or portions 24, 30 is illustrated in some further detail. In this regard, and referring initially to FIG. 7, a first or splitter stage 150 of each lane 50 of the infeed means 24 is shown. This splitter stage essentially receives articles from an aligned lane or trough-like conveyor member from the first station or location 25 and includes means for separating and thereafter handling the articles in the predetermined groups or sticks, each having a predetermined number of axially aligned, and preferably nested articles or can ends therein. It should be noted that similar structure for assuring handling of the articles in the predetermined groups or sticks is provided in similar fashion in each lane 51 of the outfeed means 30.

Figure 7:
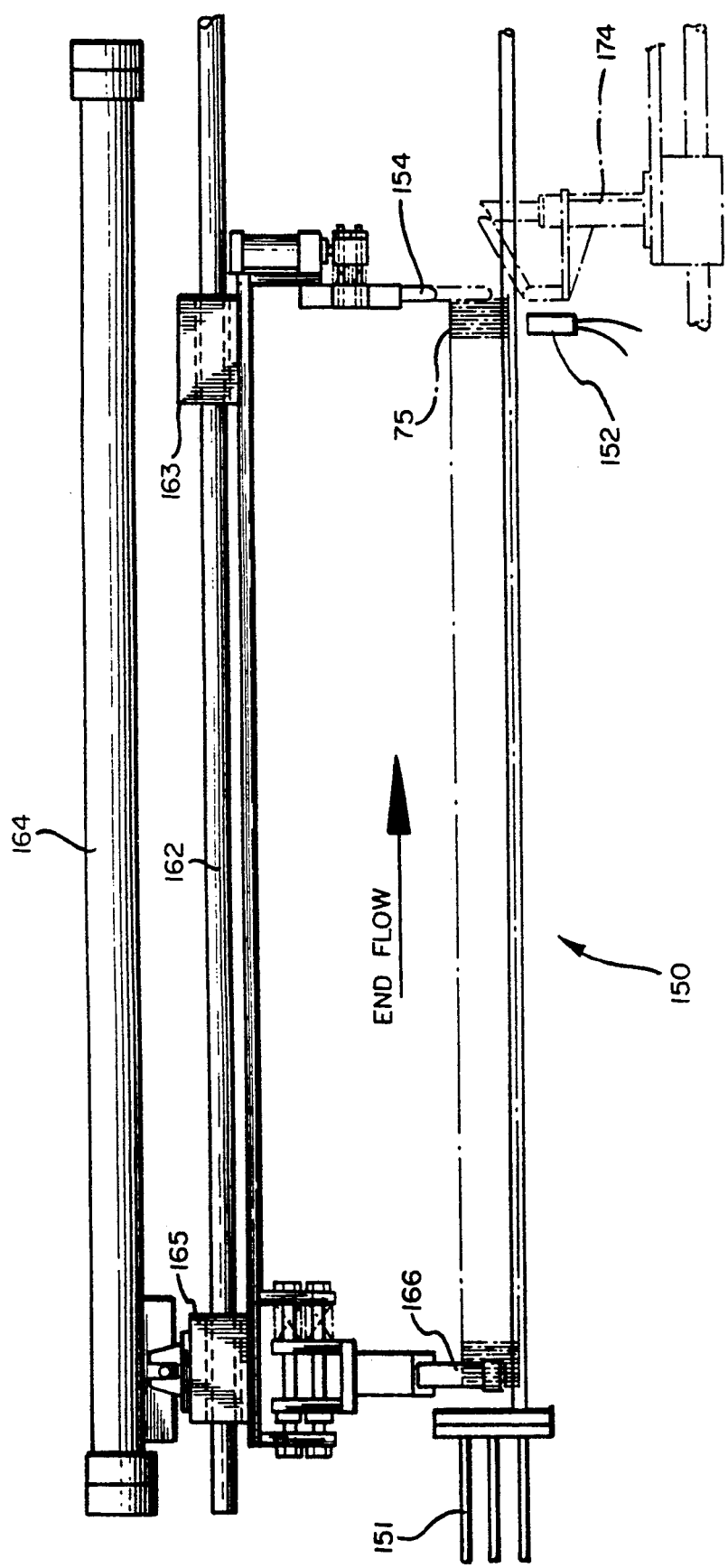
FIG. 7 is a somewhat simplified side elevation of a first stage or portion of the infeed apparatus of FIGS. 1 through 3.

In the embodiment shown in FIG. 7, ends are fed into a lane or trough portion 160 of the first infeed or splitter stage 150 by a pusher means or member 151. A sensor member 152 is preferably provided for sensing when the splitter stage 150 is filled. In this regard, the articles or can ends 75 will engage an end stop member 154, which is preferably a generally vertically oriented piston and-cylinder type member. The end stop 154 is controlled for extending and retracting in response to the signals developed by sensors such as sensor 152 along the length of the associated infeed means lane 50 as will be more fully described hereinbelow. In the embodiment illustrated, the preferred stick length is approximately 45¼ inches. As the stick is being formed in the lane 160, the end stop 154 travels along the length of the lane. For this purpose, the end stop 154 is mounted on a guide rail 162 to be driven by an Origa cylinder 164 by way of a connecting yoke 163.

Cooperatively, a gripper member or clamp 166 is spaced from the end stop 154 by approximately the desired length of the stick 75 so as to grip the rear end of the incoming stick. This clamp or gripper member 166 is similarly mounted by a similar yoke 165 to the bar or rod 162 for actuation by the same Origa cylinder 164. In this regard, the Origa cylinder utilized is similar to the one described above, but is not of the electric or "indexable" type, being rather a somewhat simpler air-type or pneumatic cylinder type, also available from the Origa Company as noted above. The clamp arrangement 166 preferably includes a blade-like end or edge portion for positively separating the stick of ends 75 from other ends following this stick in the infeed area, if and as necessary.

Figure 8:
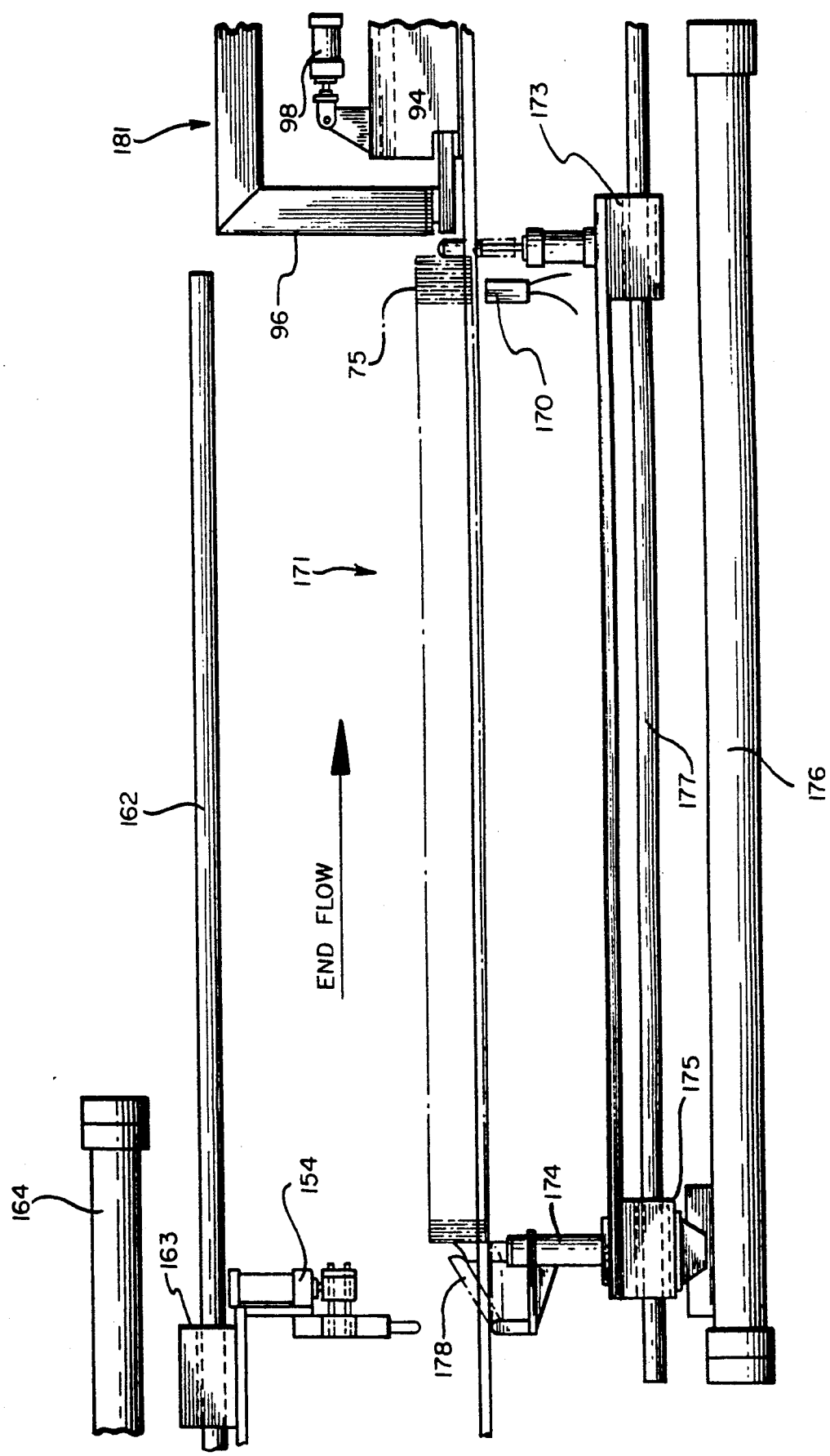
FIG. 8 is a somewhat simplified side elevation of a second stage or portion of the infeed apparatus.

A second stage 171 of the infeed device, as illustrated in FIG. 8, is provided with a similar end sensor 170, an end stop member 172, and a rear stop member 174. The end and rear stop members 172, 174 are similarly mounted on yokes 173 and 175 to be driven by a similar Origa cylinder 176 along a guide rail or bar 177. Accordingly, the timing of the respective energization of cylinders 164 and 176, as well as advancement and retraction of respective end stops 172 and 154 are controlled by the sensing of the relative position of the stick 75 by the respective sensors 152 and 170. That is, when end stop 154 and gripper 166 have advanced fully within the area defined by end stop 172 and rear stop 174, they are then and only then retracted simultaneously with advancement of end stop 172 and a spring-like return of a spring-loaded dog member 178 associated with the rear end stop member 174. This rear end stop member 174 also acts as a pusher for pushing the stick of ends, together with end stop 172 into the next or third, and final, stage 181 of the infeed means or structure, as illustrated in FIG. 9, upon actuation of Origa cylinder 176.

The stick end sensor 86, as described above with reference to the operation of the pick-and-place units is also located at this third and final portion 181 of the infeed means. It should be noted that the mounting frame structure for the pick-and-place units 80, 80a including frame members 96, 96a are somewhat diagrammatically shown in FIGS. 9 and 15. Accordingly, as the stick enters the third infeed station in FIG. 9, a pair of spring-loaded or otherwise normally closed dogs 180 (see FIG. 12) are retracted to permit passage of the stick 75 thereby, and close behind the trailing or rear end thereof. These dogs in turn permit ample space for the entry of the air cylinder 98 of the pick-and-place device as described above, and as also best viewed in the somewhat simplified partial view of FIG. 10. Thereupon, one of the pick-and-place devices may index over and lower into position around the stick of ends in the third and final infeed station 181 shown in FIG. 9, for picking up the stick 75 and eventually loading it into a tray 55 as described hereinabove.

Turning now to the outfeed station or means 30, a first stage 191 thereof shown in FIG. 16 is substantially similar to the third and final infeed stage shown in FIG. 9, with the action thereat being essentially reversed. That is, a filled gripping device or "jaws" 94a descends over the first outfeed stage and deposits a stick 75 of can ends therein. Respective end stop cylinder members or holding means 184, 186 are provided for holding the stick 75 in position upon release by jaws 94a and retraction of the pick-and-place unit 80a. The sensor 88 also indicates the presence or absence of ends in the first outfeed stage 191 of FIG. 16. These end holding means 184 and 186 are similarly mounted to an elongate rod or shaft member 190 to be driven back and forward at the proper times by an Origa cylinder 192, to deliver the stack of ends 75 to a second outfeed stage 201 shown in FIG. 17.

The second outfeed stage 201 of FIG. 17 is substantially identical in form to the second infeed station 171 of FIG. 8, but comprises essentially a mirror image thereof both in structure and operation. Accordingly, the similar parts and components of FIG. 17 are indicated by like reference numerals to those utilized in FIG. 8 with the suffix a.

The third and final outfeed stage 205, shown in FIG. 18, is in many respects similar to the first infeed stage shown in FIG. 7, and is thus labeled with like reference numerals, as to its like parts and components, with the suffix a. However, it should be noted that the end-engaging cylinder or end stop cylinder 154a is mounted on an articulated linkage 200 so that as it travels along an Origa cylinder 164a, this linkage can redirect the cylinder to accommodate a downward curve in the track of an exit chute, designated generally by reference numeral 202. This downwardly curved exit chute may be upwardly curved, curved to the side, or the like, as necessary to accommodate any offset between the end of the outfeed means or structure and any associated structure to be connected therewith for receiving the can ends. Moreover, rather than clamp means 166 as used in FIG. 7, the last stage of the outfeed end includes a second, similar end stop member 154b. This latter end stop 154b is fixed relative to end stop 154a for movement along tracks 160a and 202 in unison therewith. Each member 154a, 154b extends and retracts a suitable stop member for engaging one end of the stick as it advances into and fills the track portion 160a, the stick being guided and held during filling of track 160a by the associated end stops 172a, 174a of the second outfeed stage of FIG. 17.

Referring now again briefly to FIGS. 2 through 4, the stacking and unstacking means comprise substantially identical structures, whereby only the stacking means or apparatus 28 will be described in further detail.

The stacking means or apparatus 28, as previously mentioned, includes both the palletizing means or apparatus 56 and the scissors-like lifting and lowering apparatus 64, 66. The palletizing means or device 56 also includes a pair of similar vertical lifing and lowering assemblies or devices powered by suitable air cylinders 210, 212 which are coupled to an overhead frame member 214, 216. The entire structure is movable horizontally between the tray loading station 20 and the filled tray stacking station 26 as previously described.

In this regard, cylinders 210, 211 and 212, 213 are coupled to elongate tray gripping or pick-up bracket members 218, 220, which are configured for engaging the shoulder portion of the trays previously described, for engaging and disengaging the trays and for lifting and lowering the same relative to the stations 20, 26. The horizontal movement of the members 218, 220 between the two stations is provided by an Origa cylinder 222 similar to those already described. The Origa cylinder drives a hook-like engaging member 224 which is arranged to engage an edge of the tray 55 and to advance the same, together with the grippers 218, 220 engaged therewith from the top of the tray loading station to the top of the filled tray stacking station. At the filled tray stacking station, the lift and lowering assembly lowers the tray into position upon the filled tray stacking table 62 carried on the scissors lift assembly 66.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. An article handling system for loading articles, supplied from a first location, into trays for subsequent transport and unloading thereof, such that said system may be used for balancing a supply of articles between said first location and a second location wherein the articles are being further processed, said system comprising; a tray loading station; a plurality of infeed lanes disposed adjacent said tray loading station for receiving articles transported from the first location; a plurality of trays, each having multiple channels, and each channel being adapted to have a quantity of articles disposed therein in nested face-wise engagement; said tray loading station comprising, means for accommodating a plurality of empty ones of said trays, and for disposing one of said empty trays in position for receiving a supply of said articles, loading means comprising a plurality of generally parallel disposed pick-and-place devices each adapted to engage and thereafter discharge a stack of nested articles, operational means for said pick-and-place devices for moving said devices between a position overlying said one of said empty trays and a position overlying said infeed lanes, and control means for controlling said pick-and-place devices individually to remove stacks of nested articles from said infeed lanes until all of said pick-and-place devices have acquired a stack of nested articles, and for controlling said pick-and-place devices for operating in unison to discharge all of the articles simultaneously into said one of said empty trays.

2. A system according to claim 1, wherein said infeed lanes include means for delivering a stack of nested articles of an approximate predetermined length to a location for engagement by said loading means.

3. A system according to claim 1, wherein said loading means comprises a number of pick-and-place devices corresponding to the number of channels in one of said trays.

4. A system according to claim 1, wherein said pick-and-place devices are movable relative to said infeed lanes and wherein said operational means are operable and said control means control both said operational means and said pick-and-place devices so that any one of said pick-and-place devices can remove articles from any one of said infeed lanes.

* * * * *

UNITED STATES PATENT AND TRADEMARK OFFICE
CERTIFICATE OF CORRECTION

PATENT NO. : 5,158,424

DATED : October 27, 1992

INVENTOR(S) : Wallace W. Mojden, Andrew Mojden and Robert E. Darr

It is certified that error appears in the above-identified patent and that said Letters Patent is hereby corrected as shown below:

Column 3, Line 8 "mean" should be -- means --

Column 5, Line 34 " within " should be -- without --

Column 9, Line 54 " ar " should be -- are --

Signed and Sealed this

Second Day of November, 1993

*Attest:*

BRUCE LEHMAN

*Attesting Officer*     Commissioner of Patents and Trademarks